US00PP36037P2

(12) United States Plant Patent
Kerley et al.

(10) Patent No.: US PP36,037 P2
(45) Date of Patent: Jul. 23, 2024

(54) ***PRIMULA* PLANT NAMED 'KERANNAWIT'**

(50) Latin Name: *Primula elatior*
Varietal Denomination: KERANNAWIT

(71) Applicants: David William Kerley, Over (GB); Timothy Edward Kerley, Willingham (GB)

(72) Inventors: David William Kerley, Over (GB); Timothy Edward Kerley, Willingham (GB)

(73) Assignee: Kerley & Co., Ltd. (GB)

( * ) Notice: Subject to any disclaimer, the term of this patent is extended or adjusted under 35 U.S.C. 154(b) by 0 days.

(21) Appl. No.: 18/236,010

(22) Filed: Aug. 21, 2023

(51) Int. Cl.
*A01H 6/00* (2018.01)
*A01H 5/02* (2018.01)

(52) U.S. Cl.
USPC ..... Plt./472

(58) Field of Classification Search
USPC ..... Plt./472
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Primula elatior* plant named 'KERANNAWIT' is disclosed, characterized by abundant white double flowers, borne on Polyanthus stems. This combination of large double flowers on a Polyanthus type *Primula* is a novelty. Plants are compact, vigorous and flowers are sterile. The new variety is a *Primula elatior*, suitable for outdoor landscape and container use.

2 Drawing Sheets

Latin name of the genus and species: *Primula elatior.*
Variety denomination: 'KERANNAWIT'

BACKGROUND OF THE INVENTION

The new cultivar is the product of a planned breeding program under the direction of the inventors. The objective of the breeding program was to produce new *Primula* cultivars with abundant double flowers for commercial ornamental purposes. The new cultivar resulted from crossing of the seed parent, an unpatented, unnamed, proprietary variety of *Primula*, and the pollen parent, a different unnamed, unpatented, proprietary variety of *Primula*. The crossing resulting in the new variety was made in April of 2014 at a research greenhouse in Cambridge, United Kingdom. Selection of the new variety 'Kerannawit' was made in March of 2015, by the inventor at a research greenhouse located in Cambridge, United Kingdom.

Asexual reproduction of the new cultivar 'KERANNAWIT' was first performed in the United Kingdom during May of 2015, by tissue culture. This and subsequent propagation has shown that the unique features of this cultivar are stable and reproduced true to type in successive generations.

SUMMARY OF THE INVENTION

The cultivar 'KERANNAWIT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERANNAWIT'. These characteristics in combination distinguish 'KERANNAWIT' as a new and distinct *Primula* cultivar:

1. Double flowers.
2. White flower color.

3. Abundant flowering.
4. Flowers borne on Polyanthus stems.
5. Compact plant habit.

PARENT COMPARISONS

Plants of the new cultivar 'KERANNAWIT' are similar to plants of the seed parent, in most horticultural characteristics. However, plants of the new cultivar differ in the following ways:

1. New cultivar has double flowers; seed parent is single flowered.
2. New variety is sterile; seed parent is fertile.

Plants of the new cultivar 'KERANNAWIT' are similar to plants of the pollen parent, in most horticultural characteristics. However, plants of the new cultivar differ in the following ways:

1. New cultivar has double flowers; pollen parent is single flowered.
2. New variety is sterile; pollen parent is fertile.

COMMERCIAL COMPARISONS

Plants of the new variety can be compared to plants of the *Primula* cultivar 'Pollyanna Fresh Lemon', unpatented. Plants of the new *Primula* differed from plants of the cultivar 'Pollyanna Fresh Lemon' in the following characteristics:

1. The comparator's flower color is yellow; flower color of 'Kerannawit' is white.
2. Pedicels of 'Pollyanna Fresh Lemon' are shorter than pedicels of 'Kerannawit'.

BRIEF DESCRIPTION OF THE PHOTOGRAPHS

Figure 1:
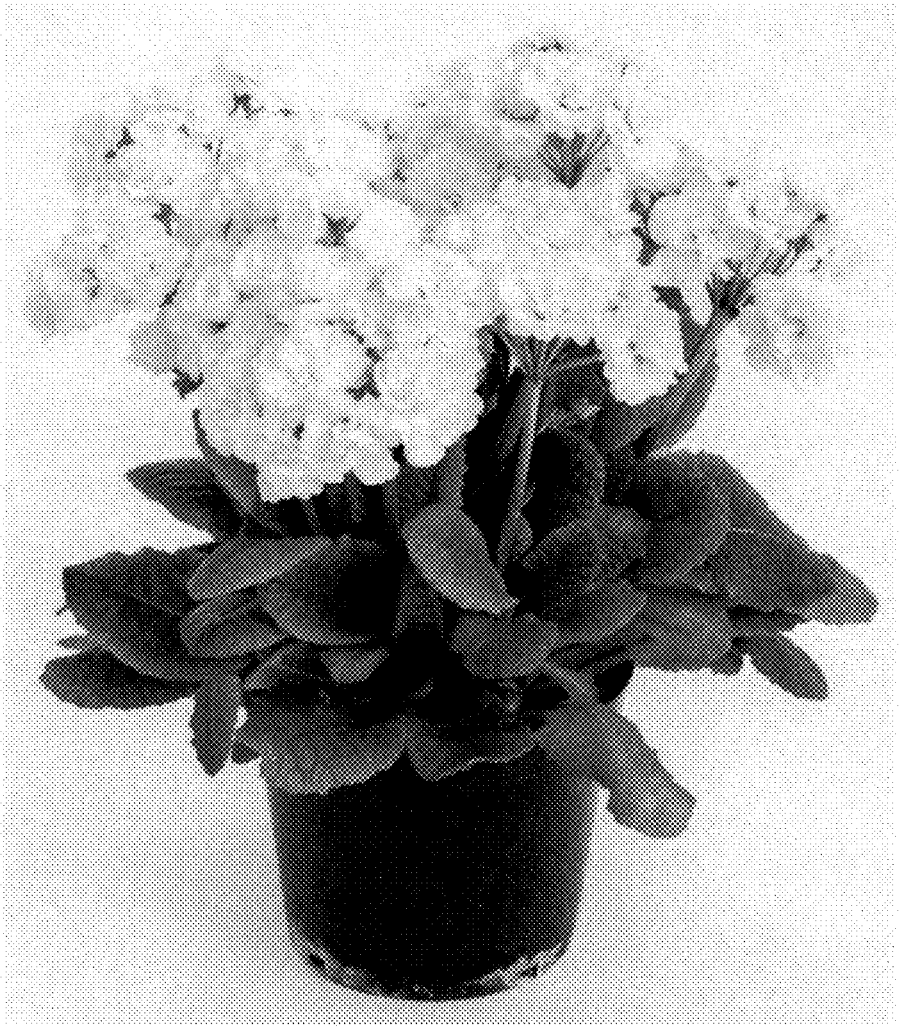

The accompanying photograph in FIG. 1 illustrates in full color a typical plant of 'KERANNAWIT' grown in Over, Cambridge, United Kingdom, in a glass-covered greenhouse. This plant was about 7 months old when the photographs were taken. During the production of the plants, day temperatures ranged from 5° to 15° C. and night temperatures ranged from 2° to 12° C.

Figure 2:
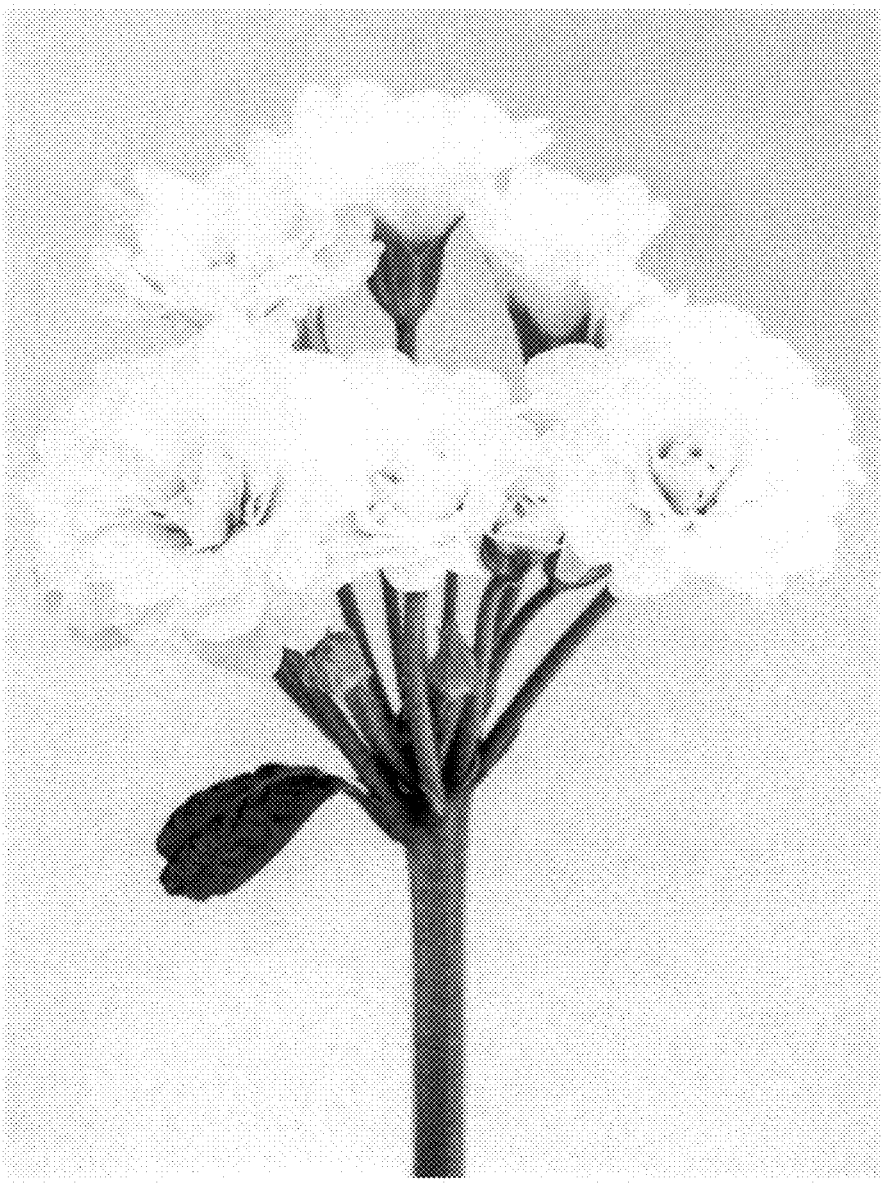

FIG. 2 illustrates a close up of a typical flower of 'KERANNAWIT'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2015 except where general terms of ordinary dictionary significance are used. The following observations and measurements describe 'KERANNAWIT' plants grown in a greenhouse in Cambridge, United Kingdom. During the production of the plants, day temperatures ranged from 1.5° C. to 25° C. and night temperatures ranged from 1.5° C. to 15° C. No chemical or photoperiodic treatments were given. Measurements were taken during Spring and numerical values represent averages of typical flowering types.

Botanical classification: *Primula elatior* 'KERANNAWIT'.

Age of the plant described: Approximately 4 to 5 months in an 11 cm pot.

PROPAGATION

Method: Tissue culture.

Time to produce a rooted plant: About 6 weeks.

Root description: Fibrous, colored near RHS White 155A.

PLANT

Plant form/habit: Upright, compact and uniform, with flowers borne on umbels above foliage.

Height: 18 cm.

Plant spread: 21 cm.

Branching characteristics: No branches, foliage emerges basally.

Vigor: Vigorous.

FOLIAGE

Leaf:

*Arrangement*.—Basal, simple.

*Length*.—11 cm.

*Width*.—4.8 cm.

*Shape*.—Oblanceolate.

*Apex*.—Obtuse.

*Base*.—Attenuate.

*Margin*.—Crenulate, undulating, slightly rugose.

*Texture of top surface*.—Glabrous, slightly rugose.

*Texture of bottom surface*.—Glabrous, prominent venation. Pubescent on veins.

*Color*.—Developing foliage upper side: Darker than RHS Yellow-Green 144A. Developing foliage under side: RHS Yellow-Green 144A. Mature foliage upper side: Near RHS Yellow-Green 146A. Mature foliage under side: Near RHS Yellow-Green 146C.

*Venation*.—Type: Pinnate. Venation color upper side: RHS Yellow-Green N148D. Venation color under side: RHS Yellow-Green N148D.

Petiole:

*Length*.—1.3 cm.

*Diameter*.—0.5 cm.

*Strength*.—Strong.

*Color*.—Upper Surface: RHS Yellow-Green 196A with blush of Purple-Pink 184A. Lower Surface: RHS Yellow-Green 196B.

*Texture upper surfaces*.—Glabrous.

*Texture lower surfaces*.—Hirsute.

FLOWER

Bloom period: Recurrent flowering during the Spring under United Kingdom outdoor conditions.

Flower type: Umbel.

Habit: Rounded double flowers borne on strong upright flower stems; flowers face upright and outward.

Persistent or self-cleaning: Persistent.

Fragrance: None.

Flowers per inflorescence: 13 to 15 flowers and buds per plant. 7 to 14 flower stems per plant.

Inflorescence size:

*Height*.—Average 13 cm.

*Diameter*.—Average 15 cm.

Flower bud:

*Height*.—1.4 cm.

*Diameter*.—0.8 cm.

*Shape*.—Ovoid.

*Texture*.—Glabrous.

*Color*.—RHS Yellow-Green 143C.

Individual flower:

*Diameter*.—4.2 cm.

*Depth*.—1.4 cm.

Petals:

*Quantity*.—46 to 52 per flower, in several concentric whorls.

*Length* (*including tube*).—2.1 cm.

*Width*.—1.5 cm.

*Shape*.—Obcordate.

*Apex*.—Emarginate.

*Margin*.—Entire.

*Texture, upper and lower surfaces*.—Glabrous.

*Color*.—Developing petals, upper surface: RHS White 157B. Developing petals, lower surface: RHS White 157D. Mature petals, upper surface: RHS White 157D. Mature petals, lower surface: RHS White 157C.

Flower throat:

*Description*.—Double flower, no open throat.

*Diameter*.—About 8 mm.

*Texture*.—glabrous

*Color*.—Near Yellow 5A (not visible in open flower)

Flower tube:

*Length*.—7 mm.

*Diameter*.—5 mm.

*Texture*.—Glabrous.

*Color*.—Near Yellow-Green 145C.

Sepals:

*Quantity*.—5 in a single whorl; fused at base.

*Length*.—1.7 cm.

*Width*.—0.5 cm.

*Shape*.—Rhomboid.

*Apex*.—Acute.

*Margin*.—Entire.

*Texture upper surfaces*.—Glabrous.

*Texture upper surfaces*.—Glabrous.
*Color, upper surface*.—RHS Yellow-Green 146D.
*Color, lower surface*.—RHS Yellow-Green 146B.

Peduncle:
*Length*.—13.6 cm.
*Diameter*.—0.6 cm.
*Orientation*.—Upright.
*Strength*.—Strong.
*Color*.—RHS Yellow-Green 195C with a blush of Grey-Red 181B.
*Texture*.—Pubescent.

Pedicel:
*Length*.—3.3 cm.
*Diameter*.—0.2 cm.
*Orientation*.—Vertical and outwards.
*Strength*.—Strong.
*Color*.—Paler than RHS Grey-Yellow 199D.
*Texture*.—Pubescent.

Bracts:
*Quantity*.—One.
*Shape*.—Narrow lanceolate.
*Length*.—0.9 cm.
*Width*.—0.2 cm.
*Apex*.—Acute.
*Color*.—RHS Yellow-Green 144A.
*Texture*.—Glabrous.

REPRODUCTIVE ORGANS

Development of reproductive organs has not been observed.

OTHER CHARACTERISTICS

Disease resistance: Plants of the new *Primula* have not been noted to be resistant nor susceptible to pathogens and pests common to *Primula*.

Temperature tolerance: Plants of the new *Primula* have been observed to have tolerated temperatures from about −5° to 28° C.

Fruit/seed production: Fruit and seed production not observed; flowers are sterile.

What is claimed is:

1. A new and distinct cultivar of *Primula* plant named 'KERANNAWIT' as herein illustrated and described.

* * * * *